United States Patent [19]

Jones et al.

[11] Patent Number: 4,963,555

[45] Date of Patent: Oct. 16, 1990

[54] FORMULATIONS OF HETEROCYCLIC COMPOUNDS

[75] Inventors: Trevor M. Jones, Sanderstead; Alan R. White, Meopham, both of England

[73] Assignee: Burroughs Wellcome Co., Research Triangle Park, N.C.

[21] Appl. No.: 317,129

[22] Filed: Mar. 1, 1989

Related U.S. Application Data

[63] Continuation of Ser. No. 825,956, Feb. 4, 1986, abandoned, and a continuation of Ser. No. 279,861, Jul. 2, 1981, abandoned, which is a continuation-in-part of Ser. No. 202,339, Oct. 30, 1980, abandoned.

[30] Foreign Application Priority Data

Jul. 18, 1980 [GB] United Kingdom ................. 8023645

[51] Int. Cl.$^5$ .............................................. A61K 31/52
[52] U.S. Cl. .................................................. 514/262
[58] Field of Search ........................................ 514/262

[56] References Cited

U.S. PATENT DOCUMENTS

| | | | |
|---|---|---|---|
| 3,592,930 | 7/1971 | Katz | 424/243 |
| 3,867,528 | 2/1975 | Ritter | 424/241 |
| 3,924,004 | 12/1975 | Chang | 424/243 |
| 3,934,013 | 1/1976 | Poulsen | 424/239 |
| 4,141,976 | 2/1979 | Voorhees | 424/240 |

FOREIGN PATENT DOCUMENTS

| | | | |
|---|---|---|---|
| 2646435 | 5/1979 | Fed. Rep. of Germany . | |
| 2847975 | 5/1980 | Fed. Rep. of Germany . | |
| 2213023 | 8/1974 | France . | |
| 1128170 | 9/1968 | United Kingdom | 514/262 |
| 1328641 | 8/1973 | United Kingdom . | |
| 1365661 | 9/1974 | United Kingdom . | |
| 1444989 | 8/1976 | United Kingdom . | |
| 1478009 | 6/1977 | United Kingdom . | |
| 2003028 | 8/1977 | United Kingdom | 514/262 |
| 1523865 | 9/1978 | United Kingdom . | |
| 1543907 | 4/1979 | United Kingdom . | |
| 2008947 | 6/1979 | United Kingdom | 514/262 |
| 1548837 | 7/1979 | United Kingdom | 514/262 |
| 1554720 | 10/1979 | United Kingdom . | |
| 1556632 | 11/1979 | United Kingdom | 514/262 |
| 1495692 | 12/1979 | United Kingdom . | |

OTHER PUBLICATIONS

Chem Abs. vol. 90, 1979, p. 396, 174691z.
Chem Abs. vol. 70, 1969, p. 248, 40621e.
Chem Abs. vol. 87, 1977, p. 331, 73318r and p. 314, 189481t.
Chem Abs. vol. 86, 1977, p. 293, 111142t.
Poulsen et al., *J. Pharm. Sci.*, 57, 928–933 (1968).
Katz et al, *J. Soc. Cosmet. Chem.*, 23(9), 565–590, (1972).
Concepts in Biochemical Pharmacology, Ed. Brodie & Gillette, 1971 Chp. 7 Katz & Poulsen.
B. J. Poulsen, et al., J. of Pharm. Sci., pp. 928–933, vol. 57, No. 6, Jun. 1968, Effect of Topical Vehicle Composition on the in Vitro Release of Fluocinolone.
M. K. Polano, et al., Arch Dermatol, vol. 112, May 1976, pp. 675–680, Dependence of Corticosteroid Penetration of the Vehicle.
J. Ostrenga, et al., J. of Pharm. Sci., pp. 1175–1179, vol. 60, No. 8, Aug. 1971, Significance of Vehicle Composition I: Relationship Between Topical Vehicle Composition, Skin Penetrability, and Clinical Efficacy.

*Primary Examiner*—Jerome D. Goldberg
*Attorney, Agent, or Firm*—Donald Brown

[57] ABSTRACT

A topical pharmaceutical formulation for use in treating virus infections of the skin or mucosa and containing 9-(2-hydroxyethoxymethyl) guanine or a salt or ester thereof which comprises a dispersed oil phase and a continuous aqueous phase containing therein water, at least 30% of a polyhydric alcohol (by weight of the formulation) and solublized acyclovir.

15 Claims, No Drawings

FORMULATIONS OF HETEROCYCLIC COMPOUNDS

This is a continuation of co-pending application Ser. No. 825,956 filed on Feb. 4, 1986 which is a continuation of of Ser. No. 279,861, filed July 2, 1981, which is a continuation-in-part of Ser. No. 202,339, filed Oct. 30, 1980, all now abandoned.

This invention relates to a topical pharmaceutical formulation suitable for use in treating virus infections of the skin and mucosa, and in particular it relates to topical formulations containing 9-(2-hydroxyethoxymethyl)guanine, otherwise known as acyclovir, and hereinafter referred to as such.

Acylovir and pharmaceutically acceptable salts and esters thereof are known to have antiviral activity against various classes of DNA and RNA viruses both in vitro and in vivo, see UK patent No. 1 523 865. In particular the compound is active against herpes simplex virus which causes herpetic keratitis in rabbits, herpetic encephalitis in mice, and cutaneous herpes in guinea pigs.

Acyclovir suffers from the disadvantage that it has a low solubility in water and is almost totally insoluble in hydrophobic solvent systems. It is accordingly difficult to produce a topical formulation containing a sufficient dissolved concentration of active ingredient for it to exert its full effect and also to optimise the flux of the compound into the skin. In addition to ease of release it is also important that any formulation of a pharmaceutically active compound should be stable for long periods of time, should not lose its potency, should not discolour or form insoluble substances or complexes, and also should not be unduly irritating to the skin or mucosa.

In example 26 of UK patent No. 1 523 865 there are listed the constituents of an oil-in-water cream containing 5% w/w acylovir, amongst which constituents is 5% w/w propylene glycol. The function of the propylene glycol in the formulation of example 26 is to act as an humectant, i.e. a hygroscopic ingredient, which should improve the cosmetic feel of the product and also limit dehydration during storage. In animal experiments this formulation and a formulation of aqueous cream B.P. (British Pharmacoepia) containing acylovir did not provide a particularly rapid cure probably because of insufficient active ingredient in solution and poor penetration of the active ingredient into the skin.

In view of the lipid nature of the skin surface, especially the stratum corneum, it has long been thought that to achieve good transdermal penetration the active ingredient in an emulsion should be located in the oil phase so that it can partition into the lipid components of the skin.

It has now been found that, in order to optimise the release of acyclovir from topical formulations, the maximum solubilised concentration of drug should be in the external phase of an oil-in-water emulsion preparation, i.e. in the aqueous phase. Further it has been found that by using a high concentration of a polyhydric alcohol as a cosolvent in the aqueous phase, for example at least 50% v/v of that phase, an increased concentration of solubilised acyclovir can be attained, leading to enhanced activity and efficacy of such formulations. Such a high concentration of a polyhydric alcohol also dispenses with the necessity of including a preservative as an additional ingredient in the formulation.

Such topical formulations also satisfy the criteria of adequate stability, maintenance of potency and are not unduly irritating to the skin or mucosa and have the advantages over the prior art formulation of penetrating skin more effectively and in greater concentration with the result that a rapid, complete cure of the infection is achieved.

According to the present invention there is provided an oil-in-water topical pharmaceutical formulation for the treatment of virus diseases of the skin or mucosa of a mammal comprising a dispersed oil phase and a continuous aqueous phase containing therein water, at least 30% of a water miscible polyhydric alcohol (by weight of the formulation) and solubilised acyclovir. Preferably the formulation contains a maximum of 50% water.

Such a topical formulation may contain 0.075% to 10% w/w acyclovir or a salt or an ester thereof, from 30% to 60% w/w of a polyhydric alcohol, from 15% to 50% w/w water and an oil phase. Hereafter references to acyclovir should be understood to include also its pharmaceutically acceptable salts and esters unless the context clearly indicates otherwise.

In a preferred aspect the formulation comprises from 1% to 10% w/w acyclovir, from 30% to 50% w/w of a polyhydric alcohol, from 20% to 40% w/w water together with an oil phase, whilst the most preferred formulation comprises from 2% to 5% w/w acyclovir, from 35% to 45% w/w of a polyhydric alcohol, from 25% to 40% w/w water together with an oil phase. The formulation should preferably contain about 40% w/w of a polyhydric alcohol.

A polyhydric alcohol is an alcohol having two or more hydroxyl groups. Polyhydric alcohols suitable for incorporation into the topical formulation of the present invention include glycols and macrogols such as propylene glycol, butane 1,3-diol, polyethylene glycol and glycerol, propylene glycol being the preferred alcohol.

When at least 50% v/v of a polyhydric alcohol is used in the aqueous phase of a formulation of the present invention, the maximum concentration of acyclovir at ambient temperature rises from 0.15% w/w, that being the maximum aqueous solubility of acyclovir, to 0.3% w/w. Thus if aqueous phase concentrations of greater than 0.3% acyclovir are incorporated into a formulation the amount of active ingredient in excess of 0.3% will be in suspension and act as a reservoir of drug. The amount of acyclovir present in the formulation should be at least sufficient to be antivirally effective and to be non-toxic. The water used in the formulation is preferably purified water, purified that is according to the standards of the British Pharmacopoeia.

The oil phase of the emulsions of this invention may be constituted from known ingredients in a known manner. While the phase may comprise merely an emulsifier (otherwise known as an emulgent), it is desirably comprised of a mixture of at least one emulsifier with a fat or an oil or with both a fat and an oil. Preferably, as explained in more detail below, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so called emulsifying ointment base which forms the oil dispersed phase of the emulsions.

Oil-in-water topical formulations may be formulated in a number of ways, all of which depend primarily on the alignment of the emulgent or emulsifying agent and emulsion stabiliser at the oil/water interface, with the non-polar or lipophilic groups soluble in the oil phase and the polar or hydrophilic or lipophilic groups in the aqueous or continuous phase. Thus the more polar hydrophilic emulgents result in oil-in-water emulsions. This principle has been systemised in the idea of a 'hydrophilic-lipophilic balance' (H.L.B.) Griffen, W. C, *J. Soc. Cos. Met. Chem.*, 1954, 5, 249 and the various emulgents have been allocated H.L.B. numbers from which their behaviour with constituents of the aqueous and oil phases (to which are applied theoretical required H.L.B. figures) may be predicted.

It is a well established theory of oil-in-water emulsion formulation that the combination of a lipophilic emulgent with a hydrophilic emulgent of the same chemical type may be used in varying proportions to give the required H.L.B. value. With the high concentration of polyhydric alcohol required to maximise acyclovir release from the formulation of the present invention an H.L.B. value of from 3.5 to 10.0, preferably 4.0 to 8.0, most preferably about 5.5, is desirable, compared with the accepted H.L.B. range for mineral oil-in-water emulsions of 8 to 18.

Emulgents and emulsion stabilisers suitable for use in the formulation of the present invention include polyoxyethylene sorbitan monostearate (polysorbate 60), sorbitan monostearate, sorbitan mono-oleate, cetostearyl alcohol, myristyl alcohol, glyceryl mono-stearate and sodium lauryl sulphate. One preferred combination of emulgents is cetostearyl alcohol and sodium lauryl sulphate in a ratio of from 3:1 to 30:1 preferably from 6:1 to 20:1, most preferably from 9:1 to 15:1.

In addition, the formulation may optionally contain other emulgents such as poloxamers in an amount of from 0.1 to 3% w/w, preferably 0.3 to 2% w/w, most preferably about 1% w/w of the formulation.

The choice of suitable oils or fats for the formulation is based on achieving the desired cosmetic properties, since the solubility of acyclovir in most oils likely to be used in pharmaceutical emulsion formulations in very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a mixed ester of 2-ethyl hexanoic acid with a blend of cetyl or stearyl alcohols known as Crodamol CAP may be used, the last three being the preferred esters. These may be used singly or in combination depending on the properties required. Alternatively, high melting point lipids such as white soft paraffin and/or liquid paraffin or other mineral oils can be used.

The present invention further provides a method for the preparation of a topical pharmaceutical formulation, as hereinbefore defined, which comprises mixing the combination of acyclovir, polyhydric alcohol and water with the oil phase.

The manner of formulating the emulsion will of course vary according to the amount and nature of the constituents, but nevertheless follows known techniques in emulsion technology (see The Pharmaceutical Codex, London, The Pharmaceutical Press, 1979). For example the acyclovir may be initially incorporated wholly in the aqueous portion where it may form a solution alone, or a mixed solution/suspension, and then emulsified with the ointment base. Alternatively where high concentrations of acyclovir are being used, a part of the aqueous portion may be formulated as an emulsion, and the balance of the water, polyhydric alcohol and acyclovir added to and dispersed into the emulsion. In another technique the acyclovir may be included in the emulsifying ointment prior to emulsification with the aqueous portion. In using these procedures, it is preferable to heat the aqueous portion and the ointment base to about 40° to 80° C., preferably 50° to 70° C., prior to emulsification which may be achieved by vigorous agitation using for example a standard laboratory mixer. Finer dispersions of the oil phase may be obtained by homogenising or milling in a colloidal mill.

A topical formulation of the present invention may be used in the treatment or prevention of viral infections caused for example by Herpes zoster, Herpes varicella and Herpes simplex types 1 and 2, which cause diseases such as shingles, chicken pox, cold sores and genital herpes. The formulation should desirably be applied to the affected area of skin from 2 to 6 times daily, preferably from 3 to 4 times.

The following are examples of the invention.

EXAMPLE 1

2% w/w Aqueous Cream

An aqueous cream was prepared from the following ingredients:

1. Acyclovir: 20.0 g
2. Cetostearyl alcohol, B.P.: 67.5 g
3. Sodium lauryl sulphate, B.P.: 7.5 g
4. White soft paraffin, B.P.: 125.0 g
5. Liquid paraffin, B.P.: 50.0 g
6. Propylene glycol, B.P.: 400.0 g
7. Purified water, B.P. to: 1000.0 g.

A part of the acyclovir (2 g) was dissolved in the water and propylene glycol at ambient temperature to produce an aqueous solution. The paraffins (4,5) and emulsifiers (2,3) were mixed together and heated to 60° C., and emulsified with the aqueous solution, also at 60°C., using a laboratory mixer at 8000 r.p.m.. The remaining acyclovir was added, the mixture dispersed, allowed to cool, and filled into lacquered aluminium tubes.

EXAMPLE 2

5% w/w Aqueous Cream

In the manner described above, an aqueous cream was prepared containing 5% w/w acyclovir.

EXAMPLE 3

0.2% w/w Aqueous Cream

1. Acyclovir: 2.0 g
2. Isopropyl myristate, B.P.: 100.0 g
3. 2-Ethylhexyl palmitate: 50.0 g
4. Light liquid paraffin, B.P.: 50.0 g
5. Cetostearyl alcohol, B.P.: 30.0 g
6. Glyceryl monostearate, B.P.: 16.0 g
7. Polysorbate 60, B.P.C.: 4.0 g
8. Propylene glycol, B.P.: 400.0 g
9. Purified water, B.P. to: 1000.0 g.

The cream was prepared in the manner described in Example 1 except that all the acyclovir was initially dissolved in the propylene glycol/water ingredients (8,9).

EXAMPLE 4

2% w/w Aqueous Cream

An aqueous cream was prepared from the following ingredients by the method described in Example 1.
1. Acyclovir: 20.0 g
2. Cetostearyl alcohol, B.P.: 67.5 g
3. Sodium lauryl Sulphate, B.P.: 7.5 g
4. White soft paraffin, B.P.: 125.0 g
5. Liquid paraffin, B.P.: 50.0 g
6. Butane 1,3-diol, B.P.: 400.0 g
7. Purified water, B.P. to: 1000.0 g.

We claim:

1. An oil-in-water topical formulation of an effective antiviral non-toxic amount of 9-(2-hydroxyethoxymethyl)guanine or a pharmaceutically acceptable salt thereof, having a dispersed oil phase and a continuous aqueous phase, said aqueous phase containing therein water, 30% to 50% w/w of a water miscible polyhydvic alcohol, and an effective antiviral non-toxic amount solubillised 9-(2-hydroxyethoxymethyl)guanine or said salt thereof.

2. A formulation according to claim 1 comprising from 1% to 10% w/w 9-(2-hydroxyethoxymethyl)guanine or said salt thereof, from 30% to 50% w/w of said propylene glycol, from 20% to 40% w/w water together with said oil phase.

3. A formulation according to claim 1 wherein said polyhydric alcohol is a glycol or macrogol.

4. A formulation according to claim 3 wherein said glycol or macrogol is selected from a group consisting of propylene glycol, butane 1,3-diol, glycerol and polyethylene glycol.

5. A method of treating or preventing viral infections of the skin or mucosa of a mammal comprising applying the topical an effective amount of the formulation according to claim 1 to the selected area of skin or mucosa from 2 to 6 times daily.

6. A method of treating or preventing Herpes simplex infections of the skin or mucosa of a mammal comprising applying the topical an effective amount of the formulation according to claim 1 to the selected area of skin or mucosa from 2 to 6 times daily.

7. A method for treating or preventing Herpes zoster infections of the skin or mucosa of a mammal comprising applying the topical an effective amount of the formulation according to claim 1 to the selected area of skin or mucosa from 2 to 6 times daily.

8. A method for treating or preventing Herpes varicella infections of the skin or mucosa of a mammal comprising applying the topical an effective amount of the formulations according to claim 1 to the selected area of the skin or mucosa from 2 to 6 times daily.

9. A topical cream comprising about 2% to about 5% w/w of micronized acyclovir or a pharmaceutically acceptable salt thereof and greater than about 30% w/w of propylene glycol.

10. A topical cream comprising about 5% w/w micronized acyclovir or a pharmaceutically acceptable salt thereof and about 40% w/w of propylene glycol.

11. An oil in water emulsion topical formulation of an effective antiviral nontoxic amount of 9-(2-hydroxyethoxymethyl)guanine or a pharmaceutically acceptable salt thereof comprising about 5% w/w of 9-(2-hydroxyethoxymethyl)guanine or a pharmaceutically acceptable salt thereof and about 40% w/w of propylene glycol in an aqueous phase thereof.

12. A method of treating a herpes viral infection of the skin or mucosa of a mammal which comprises applying to the skin or mucosa an effective herpes antiviral treatment amount of an oil in water topical formulation comprising about 5% w/w of solubilized 9-(2-hydroxyethoxymethyl)guanine or a pharmaceutically acceptable salt thereof and about 40% w/w of propylene glycol in an aqueous phase thereof.

13. An oil in water emulsion topical formulation of an effective antiviral amount of 9-(2-hydroxyethoxymethyl)guanine or a pharmaceutically acceptable salt thereof comprising about 5% w/w of 9-(2-hydroxyethoxymethyl)guanine or a pharmaceutically acceptable salt thereof and about 30 to 50% w/w of propylene glycol in an aqueous phase thereof.

14. A method of treating a herpes viral infection of the skin or mucosa of a mammal which comprises applying to the skin an effective herpes antiviral treatment amount of an oil in water topical formulation comprising about 5% w/w of solubilized 9-(2-hydroxyethoxymethyl) or a pharmaceutically acceptable salt thereof and about 30 to 50% w/w of propylene glycol in an aqueous phase thereof.

15. An oil in water emulsion topical formulation comprising 5 to 10% of 9-(2-hydroxyethoxymethyl)guanine or a pharmaceutically acceptable salt thereof and about 30 to 50% w/w of propylene glycol.

* * * * *

UNITED STATES PATENT AND TRADEMARK OFFICE
CERTIFICATE OF CORRECTION

PATENT NO. : 4,963,555

DATED : October 16, 1990

INVENTOR(S) : Trevor M. Jones; Alan R. White

It is certified that error appears in the above-identified patent and that said Letters Patent is hereby corrected as shown below:

Col. 1, line 8, (Claim 1), DELETE "solubillised", and insert therefor -- of solubilized--.

Col. 5, line 3, (claim 5), delete "the topical", and before "formulation" insert --topical--.

line 3, (claim 6), delete "the topical" and before "formulation" insert --topical--.

line 3, (claim 7), delete "the topical" and before "formulation" insert --topical--.

Col.6, line 3, (claim 8), delete "the topical" and before "formulation" insert -- topical--.

line 3-4,(claim 12), delete "herpes antiviral"; insert --anti-herpes virus--.

line 3, (claim 14), delete "herpes antiviral", and insert therefor --anti-herpes virus--.

Signed and Sealed this

Twenty-sixth Day of January, 1993

*Attest:*

STEPHEN G. KUNIN

*Attesting Officer*      *Acting Commissioner of Patents and Trademarks*